(12) United States Patent
Holland et al.

(10) Patent No.: US 8,153,118 B2
(45) Date of Patent: Apr. 10, 2012

(54) METHOD FOR ALTERING THE METABOLISM OF PLANT

(75) Inventors: Mark A. Holland, Salisbury, MD (US); Joseph C. Polacco, Columbia, MO (US)

(73) Assignees: Salisbury University, Salisbury, MD (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 11/347,579

(22) Filed: Feb. 6, 2006

(65) Prior Publication Data

US 2006/0228797 A1    Oct. 12, 2006

(51) Int. Cl.
*A01N 63/00* (2006.01)
*A01N 65/00* (2009.01)
*C12N 5/00* (2006.01)
*C12N 5/02* (2006.01)
*C12N 5/04* (2006.01)
*A01C 1/06* (2006.01)

(52) U.S. Cl. ...... 424/93.4; 424/93.1; 435/410; 435/415; 47/57.6

(58) Field of Classification Search .......... 47/57.6; 71/6; 424/93.1, 93.3, 93.4; 504/117
See application file for complete search history.

(56) References Cited

U.S. PATENT DOCUMENTS

| | | | |
|---|---|---|---|
| 5,268,171 A | 12/1993 | Polacco et al. | |
| 5,512,069 A * | 4/1996 | Holland et al. | 47/57.6 |
| 5,961,687 A | 10/1999 | Joshi et al. | |

FOREIGN PATENT DOCUMENTS

WO    WO00/60052    * 10/2000

OTHER PUBLICATIONS

Witzig et al., A Microbial Symbiont Shown to Alter the Nutritional Quality of Plants [online], Poster Presented at American Society of Plant Biologists Annual Meeting, 1999, [Retrieved Jul. 6, 2007], Retrieved from the Internet: <URL:http://faculty.salisbury.edu/~maholland/met&B12.html>.*
Witzig et al. A microbial symbiont shown to alter the nutritional quality of plants [online], Abstract of Poster Presented at American Society of Plant Biologists Annual Meeting, Jul. 1999, [Retrieved Jul. 6, 2007], Retrieved from the Internet: <URL:http://abstracts.aspb.org/pb1999/public/P51/1099.shtml>.*
Ravindra, P.R., 2000, Biotechnology Advances, 18, 459-479.*
"Enhancement of flavour biosynthesis from strawberry (*Fragaria x ananassa*) callus cultures by Methylobacterium species," Zabetakis Ioannis, Plant Cell Tissue and Organ Culture, vol. 50, No. 3, 1997, pp. 179-13.
"PPFMs and Other Covert Contaminants: Is There more to plant physiology than just plant?," Annual Review of Plant Physiology and Plant Molecular Biology Annual Reviews Inc., 1994, pp. 197-209, p. 202-p. 203.
"Occam's razor applied to 1-7 hormonology: Are Cytokimims produced by plants?" Plant Physiology, vol. 115, No. 3, Nov. 1997, pp. 865-868.
"Methanol-Utilizing Bacteria Associated with Green Plants," Dev, Ind. Microbiol., vol. 23, 1982, pp. 483-494.
Toraya et al., Applied Microbiology, Sep. 1975, pp. 477-479.
Sato et al., Applied and Env. Microbiol., Mar. 1977, pp. 515-521.
Capps et al., Jour. Bio. Chem. (1949) pp. 517-518.
Ravindra, P.R., 2000, Biotechnology Advances, pp. 18, 459-479.

* cited by examiner

*Primary Examiner* — Ruth Davis
*Assistant Examiner* — Sheridan Macauley
(74) *Attorney, Agent, or Firm* — William E. Beaumont

(57) ABSTRACT

The invention is related to a method of altering the metabolism of a plant by carrying out the steps of treating seeds of the plant with non-genetically engineered selected mutant pink-pigmented facultative methylotroph having a plant altering capability, and growing the plants from the treated seeds, wherein the plants that grow from such treated seeds exhibit an altered characteristic relative to non-treated plants.

6 Claims, No Drawings

METHOD FOR ALTERING THE METABOLISM OF PLANT

This application claims the benefit of priority date of U.S. Provisional Application No. 60/128,111, filed Apr. 7, 1999, the content of which is incorporated into the present application in its entirety.

FIELD OF THE INVENTION

The invention relates to isolating novel naturally-occurring mutant pink-pigmented facultative methylotrophs and altering a plant's metabolism with such strains by treating the plant with said strains.

BACKGROUND OF THE INVENTION

Pink-pigmented facultative methylotrophs (PPFMs) of the type *Methylobacterium mesophilicum* are bacteria normally found on plant surfaces. It has been demonstrated that these bacteria interact with plants, by 1) producing a variety of compounds that affect plant metabolism; and by 2) consuming plant metabolic waste, most notably methanol. Production compounds include, but are not limited to vitamins (Basile et al 1985. *Bryologist* 88(2):77-81.), enzymes (Holland and Polacco 1992. *Plant Physiol.* 98:942-948.), and cytokinins (Long et al 1996. In: Lidstrom and Tabita eds. *Microbial Growth on C1 Compounds*, Kluwer Academic Publishers). Strains of the bacteria have also been identified that produce amino acids (Izumi, 1985 *J. Ferment. Technol.* 63:507-513, U.S. Pat. No. 3,663,370; U.S. Pat. No. 3,907,673; U.S. Pat. No. 3,907,641 all of which are incorporated herein by reference).

The inventors have previously described a method for altering the metabolism of a plant (U.S. Pat. No. 5,268,171 herein incorporated by reference) that employs PPFMs that have been genetically engineered. The method includes engineering PPFMs to produce a product where the presence of such a product would confer desirable qualities to plants. Once identified and isolated a population of the genetically altered bacteria are placed on or near a plant targeted for improvement. Such bacteria are expected to provide their host plant with the product the bacteria are engineered to produce. The inventors also described a method that uses PPFMs to enhance seed germination (U.S. Pat. No. 5,512,069 herein incorporated by reference). The second method does not specify the genetic makeup or the origin of the PPFMs employed.

One of the inventors also described a method of treating crop plants with a spray treatment of PPFM bacteria to enhance yield (U.S. Pat. No. 5,961,687 herein incorporated by reference). By this method, the application of PPFM bacteria to flowering soybean plants in the field resulted in as great as a 70% increase in yield compared to control plants. This method does not specify the genetic makeup or origin of the PPFMs employed.

SUMMARY OF THE INVENTION

The present invention is directed to a method of altering the metabolism of a plant comprising treating plant tissues, especially seeds of the plant, with a non-genetically engineered selected mutant microorganism having a plant altering capability; and growing the plants from the treated tissue, said growing plants from the treated tissue being treated plants, said treated plants exhibiting an altered characteristic relative to non-treated plants. As a preferred embodiment of the invention, the microorganism is a pink-pigmented facultative methylotroph, the preferred tissue is a seed and the preferred plant is soybean.

The present invention is also directed to a non-genetically engineered mutant microorganism having the ability to alter plant metabolism.

The invention is further directed to plants or plant tissues that are treated with the non-genetically engineered selected microorganism.

DETAILED DESCRIPTION OF THE INVENTION

A method of the invention includes selecting variants from untreated or mutagenized PPFM populations and using them to establish "elite lines" of the bacterium. Selection, for example, could be for enhanced production of amino acids, vitamins, enzymes or cytokinins or for their efficient removal of plant products such as methanol. Variants or mutants can be selected and/or isolated by unusual physical characteristics, chemical characteristics, or by, for instance, resistance to a particular chemical or metabolite not possessed by the related or surrounding microorganism populations. Other examples of such physical or chemical characteristics include, but not limited to, the overproduction of a flavor or fragrance-enhancing compound, as well as the production of compounds that cause plant tissue regeneration in culture conditions. Other examples include the ability of the bacteria to fix atmospheric nitrogen and provide useable nitrogen to the host plant.

As used herein, "plant metabolism" is a combination of the biochemical activities of the plant and its PPFM symbiont. Thus, a plant with "altered metabolism" means a plant whose physical, biochemical or nutritional attributes have been changed due to the activities of PPFM bacteria living on it.

As used herein, with respect to a mutant that overproduces a certain compound, such as "methionine mutant", "vitamin mutant", and so on, it refers to any mutant microorganism that overproduces the product. Thusly, as used herein, "methionine mutant" refers to a mutant microorganism that overproduces methionine as compared with a normal microorganism. It can be seen that any mutant that produces a metabolite or substance that enhances the growth or otherwise affects the growth or characteristics of the associated plant is within the purview of the invention. For example, a cytokinin mutant overproduces cytokinin (e.g., zeatin or zeatin riboside) to alter the growth and regeneration of the associated plant.

As used herein, "vitamin mutant" refers to a microorganism that overproduces vitamins. Preferably, the vitamin is vitamin B-12.

As used herein, "vigor mutant" refers to a microorganism that grows well under conditions detrimental to plant growth and development. Such conditions, for example, might be low soil temperatures during spring planting.

As used herein, "triterpenoid mutant" refers to a microorganism that overproduces terpenoid compounds normally found in PPFMs or which produces novel terpenoid compounds.

As used herein, "threonine mutant" refers to a microorganism that overproduces the amino acid threonine.

As used herein, "L-glutamic acid mutant" refers to a microorganism that overproduces the amino acid L-glutamic acid.

As used herein, "L-lysine mutant" refers to a microorganism that overproduces the amino acid L-lysine.

As used herein, "a single-cell protein mutant" refers to a microorganism that contributes to the nutritional quality of its plant host by overproducing a high quality, nutritionally complete protein. Single cell protein is a high quality protein produced by a microorganism, and is used directly as a food supplement in animal feeds or by people. In certain instances, the microorganism is used directly for food because of its nutritional qualities.

As used herein, "a mutant that over-produces the amino acids L-lysine, L-aspartic acid, L-alanine, L-valine, L-leucine, and L-arginine" has the characteristic of overproducing all of the above-named amino acids.

The invention is not limited to *Methylobacterium mesophilicum*. For example, microorganisms that can be used in the invention include any other pink-pigmented facultative methylotrophs (PPFMs). Preferably, PPFM includes, but is not limited to, *Methylobacterium mesophilicum, Methylobacterium organophilum, Methylobacterium extorquens, Methylobacterium fujisawaense, Methylobacterium radiotolerans, Methylobacterium rhodesianum, Methylobacterium rhodinum,* or *Methylobacterium zatmanii*. In the most preferred embodiment, the microorganism is *Methylobacterium mesophilicum*.

The type of plants that can be altered by the method of the invention include, but not limited to, nonvascular plants, vascular plants, gymnosperms, angiosperms, dicots, or monocots. Preferably, the plant belongs to the vascular plants. More preferably, the plant is an angiosperm. Most preferably, the plant is soybean.

In the seed treatment method of the invention, the treatment method can be any method so long as the microorganism is able to bind to the seed. Such a method may include taking dry plant seeds and soaking them in suspensions of washed cells of the mutants, preferably for about 6 hours, and allowing the seeds to imbibe the mutant bacteria. Following this treatment, the seeds can be planted as normal to produce treated plants. Control seeds also can be planted to produce control plants. Harvested tissue from the treated plants is assayed for increased amounts of Vitamin B-12 as compared with control plants. Another treatment method may utilize electricity to cause the microorganism to adhere to the plant seed. Another method may use the PPFMs as a seed coating or powdered inoculum.

The introduction and transfer of the non-genetically altered or engineered strains can be accomplished by several methods. For example, cured or uncured seed can be imbibed in bacterial suspensions. Alternatively, cured or uncured scions can be grafted onto bacteria associated stocks pursuant to well known methods practiced in agriculture. Bacterial-associated embryos can be propagated under cell culture isolation that induces plantlet formation. Plant tissue cultures can be co-cultivated with, or inoculated with the bacteria. Another method capable of introducing and transferring the communal bacterium to the host plant is to vacuum infiltrate bacteria into seedlings or somatic embryos. Plant cuttings could be rooted in water or nutrient solutions containing bacteria. Finally, plants could be sprayed with a suspension of bacterial cells.

As used herein, "non-genetically engineered" PPFM mutant means any mutant that is isolated from a natural sample, and thus called "naturally occurring". Alternatively, the mutant may be subject to a mutagenizing amount of chemicals, irradiation, or stress such that the microorganism exhibits an altered metabolism phenotype. The phenotype may be, but not limited to, overexpression of various nutritional compounds, such as vitamins or amino acids.

Various prior art methods of genetically altering bacteria can be used in accordance with the present invention. For example, spontaneous and induced mutants can be recovered and selected for resistance to a series of antibiotics, such as pipericillin, rifampicin, etc. If desired, multiple resistances can be assembled.

An alternate approach for obtaining the bacteria is to recover bacteria that have acquired promiscuous plasmids bearing drug resistance (gene conferring drug inactivation) by non-genetically engineered methods.

Another method of altering the bacteria is to recover bacteria resistant to, or able to inactivate herbicides such as glyphosate and sulfonyl urease which inhibit the 5-enolpyruvylshikimic acid-3-phosphate synthase and acetolactate dehydrogenase, respectively.

Once bacterial strains are selected, seeds of plants can be soaked in suspensions containing these strains and allowed to imbibe bacterial cells. Such treated seeds can be planted. Mature plant and seed products can be harvested and tested for increases in such compounds as certain desired amino acids, vitamins, enzymes or cytokinins. Isolated PPFMs growing under extreme conditions might also impart superior hardiness or vigor to plants grown from seed imbibed or inoculated with such PPFMs.

OTHER MUTANTS

The application of selected strains of PPFM bacteria to plants for the purpose of altering their metabolism will be useful as a technology only to the extent that PPFMs produce a variety of products of interest or which may be manipulated. In fact, a number of useful strains have already been described for other purposes and are included here to serve as examples of the type of mutant PPFM cell lines that can be made, such as: *Methylobacterium rhodinum* (ATCC# 43282) over-produces the amino acid threonine; *Methylobacterium* sp. (ATCC# 21371) over-produces the amino acid L-glutamic acid; *Methylobacterium* sp. (ATCC# 21372) over-produces the amino acid L-glutamic acid; *Methylobacterium* sp. (ATCC# 21926) over-produces the amino acid L-lysine; *Methylobacterium* sp. (ATCC# 21969) over-produces the amino acid L-glutamic acid; *Methylobacterium* sp. (ATCC# 21927) over-produces the amino acids L-lysine, L-aspartic acid, L-alanine, L-valine, L-leucine, and L-arginine; and *Methylobacterium* sp. (ATCC# 21438) produces single-cell protein.

PPFM bacteria are also documented to produce triterpenoid compounds, which is significant because these might be implicated in development of novel flavors and fragrances or condition pest resistance (Bisseret, P., Zundel, M., Rohmer, M. 1985. *Eur. J. Biochem.* 150:29.; Renoux, J. M., Rohmer, M. 1985. *Eur. J. Biochem.* 151:405.; Zundel, M., Rohmer, M. 1985. *Eur. J. Bioch.* 150:35.)

EXAMPLES

Example 1

Boosting Methionine Content in Soybeans

Mutant PPFMs (methionine mutant 1) were isolated from the general population of PPFMs by their resistance to the methionine analog ethionine. Phenotypes of putative variants or mutants were confirmed as methionine-excreting and over-producing by their ability to support the growth of an *E. coli* methionine auxotroph. This organism was deposited with the American Type Culture Collection, (ATCC), 10801 University Boulevard, Manassas, Va., 20110, USA, under provisions of the Budapest treaty and assigned ATCC 202213. The deposit will be maintained for the life of the patent as required by Treaty. All restrictions imposed by the depositor on the availability to the public of ATCC 202213 will be irrevocably removed upon granting the patent. Dry soybean seeds were soaked for 6 hours in suspensions ($10^9$ cells/ml) of mutant cells washed in 0.5% saline, allowing the seeds to imbibe the mutant bacteria. A duplicate set of dry soybean seeds were soaked in non-mutant isolates of PPFMs (control) designated as ATCC 202211.

Following this treatment, all seeds were planted as normal to produce treated plants and control plants. Beans harvested from the treated plants and control plants were sent to an independent laboratory for analysis. It was determined that seeds harvested from the plants treated with the mutant strain exhibited a 12% increase in methionine content over control levels.

Example 2

Boosting Methionine Content in Soybeans

The experiment above was duplicated using a second strain of methionine secreting and overproducing PPFMs (methionine mutant 2). This organism was deposited with the American Type Culture Collection (ATCC), 10801 University Boulevard, Manassas, Va., 20110, USA, under provisions of the Budapest treaty and assigned ATCC 202212. The deposit will be maintained for the life of the patent as required by Treaty. All restrictions imposed by the depositor on the availability to the public of ATCC 202212 will be irrevocably removed upon granting the patent. Dry soybean seeds were soaked in suspensions of washed cells of the mutant for 6 hours, allowing the seeds to imbibe the mutant bacteria. A duplicate set of dry soybean seeds were soaked in non-mutant isolates of PPFMs. Plants from seeds thus treated produced seeds exhibiting an 8% increase in methionine content over control seeds.

Example 3

Increasing the Vitamin Content of Plants

Vitamin B12 is an essential nutrient for human health. Normally, it is made by intestinal bacteria and absorbed through the gut. Alternatively, it is found in meat. Plants are not a source of the vitamin and it has been questioned whether plants require it themselves. However, several enzymes that include a B12 co-factor have been reported in plants (Poston, J M 1977. *Science* 195:301.; Poston, J M 1978. *Phytochemistry* 17:401.) and B12 produced by *Methylobacterium* (PPFM bacteria) was reported to stimulate the growth of liverworts in culture (Basile, D. V., Basile, M. R., Li, Q. Y., Corpe, W. A. 1985. *Bryologist* 88(2):77.) Since B12 is extremely light labile, it seems likely that plants do not accumulate large quantities of it even though it is normally present in their tissues (Nelson, D. L., Cox, M. M. 2000. *Lehninger Principles of Biochemistry*. $3^{rd}$ edition, Worth.).

We selected naturally-occurring mutants of PPFM bacteria that overproduce vitamin B12 based on their ability to stimulate the growth of *Arthrobacter* (ATCC#12834), a B12 auxotroph. Thirty-six putative mutants were initially selected; that number was reduced to 17 upon re-screening. Culture supernatants from these isolates were assayed for vitamin B12 content by the microbiological method of Capps et al. (Capps, Hobbs, Fox. 1949 *J. Biol. Chem.* 178:517.) using a commercial B12 assay medium (Difco #0360) and *Lactobacillus delbrueckii* subsp. *Lactis* ATCC# 4797. The results of this assay are shown in Table 1 for 17 selected strains of PPFM.

TABLE 1

Vitamin B12 content of PPFM culture supernatants (ng vit. B12/ml culture medium)

| Strain # | ng B12/ml |
|---|---|
| 1 | 5.4 |
| 2 | 4.2 |
| 4 | 5.8 |
| 5 | 5.7 |
| 6 | 5.9 |
| 7 | 6.2 |
| 8 | 6.9 |
| 9 | 6.5 |
| 10 | 7.5 |
| 11 | 15.0 |
| 13 | 5.5 |
| 15 | 7.5 |
| 21 | 8.0 |
| 26 | 4.2 |
| 29 | 5.0 |
| 32 | 6.0 |
| 34 | 4.9 |

Among the B12 over-producing mutants isolated, #11, as shown in Table 1, was a standout, producing three times the amount of B12 produced by the other isolates. This organism, designated *Methylobacterium* mutant B12-11, was deposited with the American Type Culture Collection (ATCC), 10801 University Boulevard, Manassas, Va., 20110, UA, on Apr. 4, 2000, under provisions of the Budapest Treaty. The deposit is designated PTA-1561. The deposit will be maintained by the depositor and the restrictions on the availability to the public of this strain will be irrevocably removed upon the granting of the patent. We tested mutant B12-11 on plant tissue to see whether it could increase the B12 content of the plant.

Seeds of leaf lettuce, *Lactuca sativa* cv. Green Ice (Burpee Seed Co.) were heated in a dry oven at 50° C. for 48 hours to reduce the resident PPFM bacteria population. Following this treatment, they were imbibed in a suspension of mutant B12-11 cells for six hours (the method is as described for the methionine over-producing mutants described above), then planted in the greenhouse. A second set of seeds was imbibed in mutant B12-11 cells, but was not heated before imbibition. Control plants were not heated, nor were they imbibed in cells of the mutant. After one month of growth, leaf tissue was harvested from the plants and aqueous extracts were prepared from them. These extracts were assayed for Vitamin B12 content as described above. B12 was not detected in control plants, but measured about 0.1 µg/gram fresh weight lettuce in the heat-treated seeds and about 0.01 µg/gram fresh weight lettuce in the unheated seeds. This is a very small amount of the vitamin to be sure, but given the fact that the recommended daily allowance of B12 is only 2 µg for adults, it is significant.

These effects are not limited to leaf lettuce. Soybean is also expected to accumulate B12 in bean tissue to even higher levels than in leaf lettuce.

Example 4

Plants of Induced Vigor

Seeds of crop plants frequently germinate and grow poorly under cold, wet field conditions early in the spring. Because PPFM bacteria influence both the rate of germination and growth, PPFMs that grow under lower than normal temperatures are selected. Selection includes isolating surviving organisms grown at 4° C. When these PPFMs and added to seeds, enhanced vigor can be expected from the plants grown from these seeds.

Example 5

Cytokinin Over-Producing Plants

PPFMs overproducing cytokinins are selected for example, by their ability to stimulate growth of plant cells in culture. Once isolated, the PPFMs are placed in seeds, and plants are grown from such seeds to verify overproduction of the cytokinins by the plants. Such plants are expected to display superior growth and yield characteristics compared to untreated plants.

Alternatively, PPFMs that overproduce cytokinins are sprayed on plants during flowering to enhance yield. The effectiveness of this strategy was demonstrated in U.S. Pat. No. 5,961,687 using unselected lines of PPFMs. Selected mutant lines of the PPFMs are expected to be even more effective.

Example 6

Plants Producing Unusual Products

It is known that PPFMs produce unusual products such as triterpenoid compounds. Isolating PPFMs producing such compounds and inoculating plant tissues with them generate plants that contain the triterpenoid. This practice is used to overproduce other compounds. For example, Zabetakis (1997. Plant, Cell, Tissue and Organ Culture 50:179-183.) found that tissue cultures of strawberry that did not include PPFM bacteria did not synthesize furanones, molecules that participate in the synthesis of strawberry flavor and fragrance compounds. When the same cultures were inoculated with PPFMs, flavor and fragrance compounds were made. This work did not employ selected lines of PPFM bacteria.

Selected PPFM mutants are expected to confer on cell cultures or whole plants the ability to make compounds that they do not normally make or to make greater quantities of compounds (like flavor or fragrance components) that they normally make at low levels.

Example 7

Enhancement of Tissue Culture Performance

Corpe and Basile (1982. Dev. Indust. Microbiol. 23:483.) reported that tissue cultures of *Streptocarpus gracilis* that were inoculated with PPFMs regenerated plantlets while similar cultures growing without the bacteria did not regenerate. Their work did not employ selected lines of PPFM bacteria. The performance of plant cell cultures with respect to growth and regeneration is expected to be greatly enhanced by the inclusion of selected PPFM mutants.

Example 8

Bacterial Contributions to Plant Nitrogen Metabolism

Many of the PPFM bacteria contain a nitrogenase enzyme with which they convert atmospheric nitrogen gas into a usable form. To test whether any of this fixed atmospheric nitrogen contributes to the nitrogen metabolism of plants inhabited by nitrogen-fixing PPFMs, we performed the following experiment.

Seeds of tobacco (*Nicotiana tabacum*) were heated at 50° C. for 48 hours to reduce their resident PPFM population. The treated seeds were then sown on 15% agar in distilled water or on 15% agar in distilled water to which a nitrogen source was added. Untreated (control) seeds were sown on the same two media. The seeds were grown under continuous light for two weeks, during which time they were observed for signs of nitrogen deficiency. At the end of this time, chlorophyll content of the seedlings was measured, chlorosis being indicative of nitrogen deprivation. Seedlings grown on nitrogen containing medium, whether with or without normal levels of PPFM bacteria showed normal growth and color development. In contrast, seeds with normal levels of PPFM bacteria growing on medium without added nitrogen were smaller and contained only 55% as much chlorophyll as plants grown on nitrogen. Significantly, seedlings with low numbers of PPFMs growing on nitrogen-free medium not only grew very slowly, but contained only 29% as much chlorophyll as seedlings grown on nitrogen. These results suggest that nitrogen fixation by the PPFMs can help to support the growth of plants. Selected cell lines of PPFMs are expected to contribute nitrogen to their host plants to an even greater extent.

From the above experiments and working examples, applicant has demonstrated broad utility of the invention. Thus, the invention is not limited to the examples and disclosure, which serve purposes of illustration. Rather, the invention is limited by the scope of the appended claims.

What is claimed is:

1. A method of producing a plant which contains vitamin B-12 therein, comprising the steps of:
   a) treating plant tissue with an isolated pink-pigmented facultative methylotroph mutant that produces vitamin B-12, thereby imparting vitamin B-12 from the methylotroph into the plant tissue, wherein the mutant is *Methylobacterium* mutant B12-11 having accession number ATCC PTA-1561; and
   b) growing the plant from the treated tissue, whereby the plant contains vitamin B-12.

2. The method of claim 1, wherein said plant is a soybean plant.

3. The method of claim 1, wherein said plant is leaf lettuce.

4. The method of claim 1, wherein said tissue is a seed.

5. The method of claim 1, wherein the treating plant tissue comprises the step of soaking seeds in a suspension of washed cells of the mutant B12-11, thereby allowing seeds to imbibe the washed cells.

6. The method of claim 1, wherein the treating plant tissue comprises the step of spraying a suspension of cells of mutant B12-11 on the plant while growing.

* * * * *